US012805808B2

(12) United States Patent
Kangas et al.

(10) Patent No.: US 12,805,808 B2
(45) Date of Patent: Nov. 24, 2026

(54) TECHNIQUES FOR NOISE REDUCTION

(71) Applicant: Oura Health Oy, Oulu (FI)

(72) Inventors: Mika Petteri Kangas, Oulu (FI); Jaakko Tapio Vartiainen, Oulu (FI); Jukka Tapani Mäkinen, Oulu (FI); Kirsi Marja Maansaari, Oulu (FI); Olli Petteri Heikkinen, Oulu (FI); Pekka Karhula, Oulu (FI)

(73) Assignee: Oura Health Oy, Oulu (FI)

( * ) Notice: Subject to any disclaimer, the term of this patent is extended or adjusted under 35 U.S.C. 154(b) by 325 days.

(21) Appl. No.: 18/422,914

(22) Filed: Jan. 25, 2024

(65) Prior Publication Data

US 2025/0241595 A1 Jul. 31, 2025

(51) Int. Cl.
*A61B 5/00* (2006.01)
*A61B 5/0205* (2006.01)

(52) U.S. Cl.
CPC .......... *A61B 5/7203* (2013.01); *A61B 5/0086* (2013.01); *A61B 5/0205* (2013.01); *A61B 5/6802* (2013.01); *A61B 5/6826* (2013.01)

(58) Field of Classification Search
CPC ... A61B 5/7203; A61B 5/0086; A61B 5/0205; A61B 5/6802; A61B 5/6826; A61B 5/0002; A61B 5/01; A61B 5/02055; A61B 5/02416; A61B 5/4806; A61B 5/7214; A61B 5/145
See application file for complete search history.

(56) References Cited

U.S. PATENT DOCUMENTS

2016/0113529 A1* 4/2016 Aoyagi .............. A61B 5/02108 600/480
2017/0119266 A1* 5/2017 Wong ................... A61B 5/7246

* cited by examiner

*Primary Examiner* — Abid A Mustansir
(74) *Attorney, Agent, or Firm* — ArentFox Schiff LLP

(57) ABSTRACT

Methods, systems, and devices for wavelength based noise filtering for a wearable ring device are described. For example, a noise filtering process may involve combining multiple wavelengths with different penetration depths. For instance, a first measurement may include a first signal gathered from emitting a first light and a second light. A second measurement may include a second signal gathered from emitting the first light and a third light. That is, the first light may be a common denominator between the two measurements. The wearable device may compare or contrast the different signals to determine a noise component. The wearable device may determine the noise component based on the differences between the measurements and their associated penetration depths. The device may then remove the noise component (e.g., filter the noise) from the first and second signals resulting in a clean signal.

20 Claims, 7 Drawing Sheets

TECHNIQUES FOR NOISE REDUCTION

FIELD OF TECHNOLOGY

The following relates to wearable devices and data processing, including techniques for wavelength-based noise reduction.

BACKGROUND

Some wearable devices may be configured to collect data from users associated with physiological phenomena, motion artifacts, or both, such as heart rate, oxygen saturation level, blood pressure, or the like. However, physiological features of a user's tissue (e.g., different layers of tissue, bone, reflections from blood vessels, etc.) may cause noise within acquired physiological measurements. As such, there are technical challenges with removing the noise leading to inaccurate physiological data.

DETAILED DESCRIPTION

Figure 1:
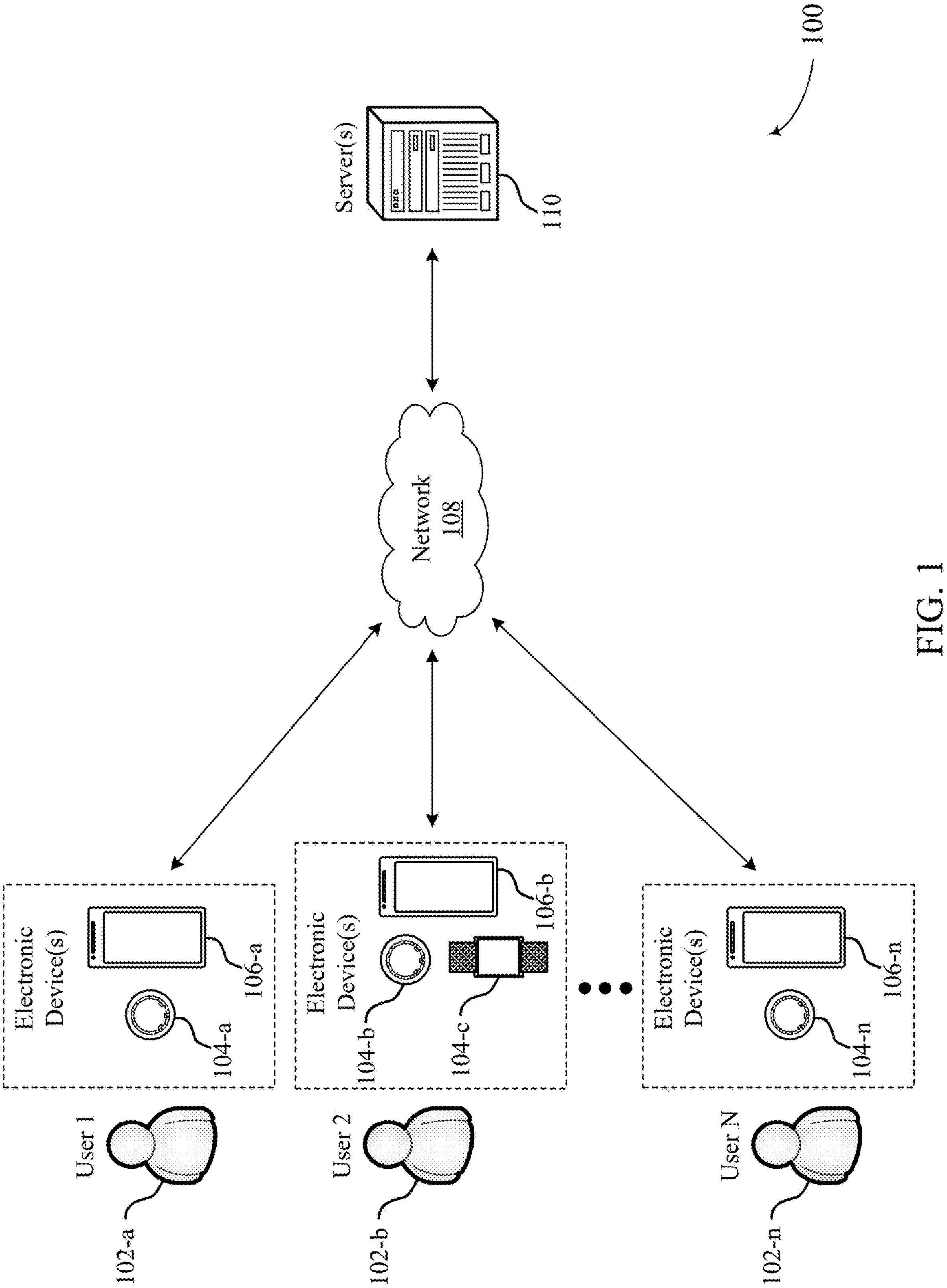
FIG. 1 illustrates an example of a system that supports techniques for noise reduction in accordance with aspects of the present disclosure.

Some wearable devices may be configured to collect data from users associated with movement and other activities. For example, some wearable devices may be configured to continuously acquire physiological data associated with a user including temperature data, pressure data, heart rate data, and the like. In order to efficiently and accurately track physiological data, a wearable device may be configured to collect data continuously while the user wears the device.

Measurements from different sensors of a wearable device may vary. For example, physiological data, mobility measurements, or both, from a wearable device may be subject to noise from the variability in the different sensors. There may be different types of noise, such as hardware noise, physiological noise, and environmental noise. Hardware noise may include noise that is attributable to sensors used to acquire physiological data. Comparatively, physiological noise may be attributable to physiological characteristics/features of a user's tissue (e.g., different layers of tissue, bone, reflections from blood vessels, etc.), that may cause noise within acquired physiological measurements (e.g., light reflecting from a blood vessel). Environmental noise may include noise attributable to an environment of the user, such an external light that interferes with a signal from light emitting elements of the wearable device. The different types of noise may cause inconsistencies in the processing of the data, mobility measurements, or both.

Additionally, measurements performed at different tissue penetration depths (e.g., measurements performed with different colored light emitting diodes (LEDs), where different colors/wavelengths penetrate tissue to different penetration depths), may result in different noise components at each depth. Thus, one or more sensors of a wearable device (e.g., a ring, watch, necklace, earring, or any other wearable device placed on a human body part) may be calibrated to accurately collect physiological data. However, the calibration process may not isolate some aspects of noise from the other types of noise, which may cause the sensors to be improperly calibrated. For example, physiological measurements may be based on blood flow within an artery at a first depth, but may be impacted by noise from a different (e.g., shallower) penetration depth. A lack of proper calibration may lead to inaccurate or misleading physiological data or a negative experience for the user of the wearable device.

Accordingly, techniques described herein are directed to devices, methods, and systems for a noise filtering process used to improve the physiological measurement accuracy of a wearable device. In some examples, the noise filtering process may involve combining multiple wavelengths used to collect signals for physiological data. Different colored emitted light may produce wavelengths capable of different penetration depths. For instance, a first measurement may include a first signal gathered from emitting a first light and a second light (e.g., light from a green LED and a red LED, respectively). A second measurement may include a second signal gathered from emitting the first light and a third light (e.g., light from the green LED and an IR LED, respectively). That is, the first light (e.g., the green LED) may be a common denominator between the two measurements. Further, the first light may model skin-ring motion and include one or more motion artifacts attributable to motion of the user/wearable device.

In some cases, the wearable device may perform physiological measurements (e.g., blood oxygen saturation (SPo2) and/or heart rate measurements) as part of the first measurement and the second measurement. The wearable device may compare and/or contrast the different physiological measurements (e.g., signals) to determine a noise component. For instance, noise attributable to green light may be common across the respective signals. The wearable device may determine the noise component based on the differences between the physiological measurements and their associated penetration depths. The device may then remove the noise component (e.g., filter the noise) from the previous measurements (e.g., signals) resulting in a clean signal. Stated differently, the device may determine noise attributable to the green light across both signals (due to green light being the common denominator across both signals), and thereby remove the common noise and improve the quality of the signals, and therefore improve the quality/accuracy of physiological data associated with the acquired signals.

Aspects of the disclosure are initially described in the context of systems supporting physiological data collection from users via wearable devices. Aspects of the disclosure are further illustrated by and described with reference to apparatus diagrams, system diagrams, and flowcharts that relate to wavelength-based noise reduction.

FIG. 1 illustrates an example of a system 100 that supports techniques for noise reduction in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols. Moreover, in some cases, the wearable device 104 and the user device 106 may be included within (or make up) the same device. For example, in some cases, the wearable device 104 may be configured to execute an application associated with the wearable device 104, and may be configured to display data via a GUI.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2)

circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for using measurements from different wavelengths to filter a noise component from one or more measurements of one or more physiological phenomenon of a wearer (e.g., a user 102) of a wearable device 104. For example, physiological data, mobility measurements, or both, from a wearable device 104 may be subject to noise from the variability in the different sensors, such as the penetration depths measured by the respective sensors. For instance, measurements performed at different tissue penetration depths may result in different noise components at each depth. The wearable device 104 may implement a noise filtering process to improve the physiological measurement accuracy of the wearable device 104.

For example, in some cases, the wearable device 104 may measure a first signal gathered from emitting a first light (e.g., green light) and a second light (e.g., red light). Additionally, or alternatively, the wearable device 104 may measure a second signal gathered from emitting the first light (e.g., green light) and a third light (e.g., IR light). Each of the respective lights/wavelengths may penetrate the tissue of the user 102 to different penetration depths, and may therefore exhibit different noise components due to the different penetration depths/tissue being measured.

Continuing with the same example, the wearable device 104 may compare the different signals to determine noise components within the respective signals. The wearable device 104 may determine the noise component(s) based on the differences between the physiological measurements and their associated penetration depths. For instance, due to the fact that green light was used to acquire both signals, the wearable device 104 may identify a noise component within both signals that is attributable to the green light. The wearable device 104 may then remove the noise component (e.g., filter the noise) from the respective signals resulting in clean signals. In other words, the wearable device 104 may filter out the noise components attributable to green light that is common across both signals.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
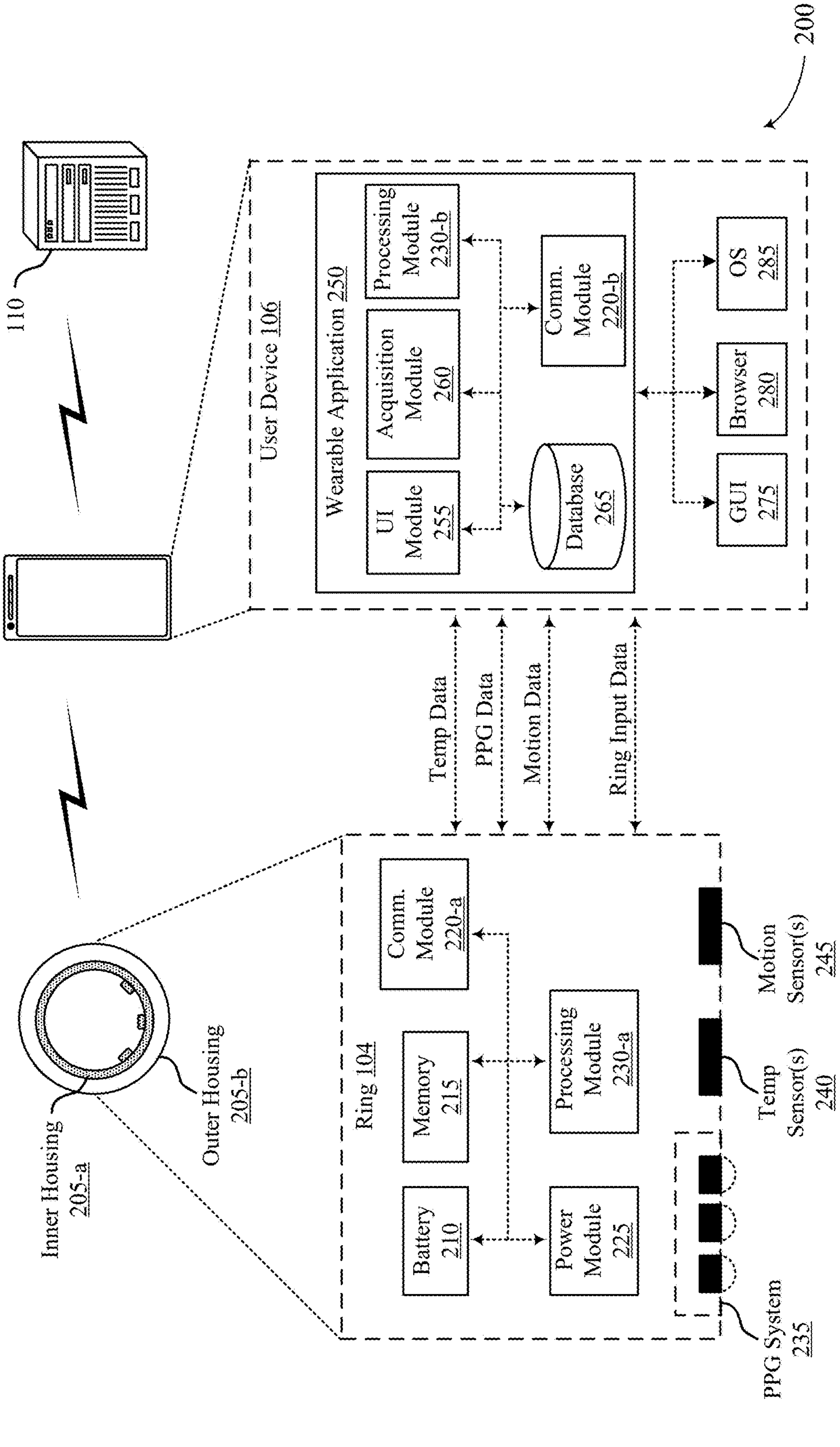
FIG. 2 illustrates an example of a system that supports techniques for noise reduction in accordance with aspects of the present disclosure.

FIG. 2 illustrates an example of a system 200 that supports techniques for noise reduction in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG LEDs. In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the IR spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

In some cases, the wearable device 104 and the user device 106 may be included within (or make up) the same device. For example, in some cases, the wearable device 104 may be configured to execute the wearable application 250, and may be configured to display data via the GUI 275.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for using different wavelengths to filter a noise component using one or more measurements from a set of light emitting elements and a set of photodetectors of a wearable device 104. In some cases, the light emitting elements include LEDs, as described with reference to the PPG system 235. For example, physiological data, mobility measurements, or both, collected via a wearable device may be subject to hardware noise from the variability in the different sensors (e.g., sensors of the PPG system 235), physiological noise attributable to physiological features of a user's tissue (e.g., variability in the optical signal response at different physiological layers/structures seen with different light penetration depths), as well as environmental noise attributable to characteristics of the user's surrounding environment.

For instance, light associated with different wavelengths (e.g., different colors, such as green light, red light, IR light, etc.) may penetrate a tissue of a user 102 to different penetration depths. Measurements performed at different tissue penetration depths (e.g., using different wavelengths) may result in different noise components at each depth. In this regard, wearable devices 104 described herein may implement a noise filtering process to improve the physiological measurement accuracy by combining multiple wavelengths, identifying common noise components across different signals, and filtering out the common noise components.

For example, a wearable device 104 may measure a first signal using a first light (e.g., green light) and a second light (e.g., red light). Additionally, or alternatively, the wearable device 104 may measure a second signal using the first light (e.g., green light) and a third light (e.g., IR light). Each of the respective lights/wavelengths may penetrate the tissue of the user 102 to different penetration depths, and may therefore exhibit different noise components due to the different penetration depths/tissue being measured.

Continuing with the same example, the wearable device 104 may compare the different signals to determine noise components within the respective signals. In particular, the wearable device 104 may compare the signals to identify a common noise component that is attributable to green light, which is a common denominator between the two respective signals. The wearable device 104 may determine the common noise component based on the differences between the signals and their associated penetration depths. The wearable device may then remove the noise component (e.g., filter the noise) from the previous measurements resulting in clean signals. In other words, the wearable device 104 may filter out the noise components attributable to green light that is common across both signals.

Figure 3:
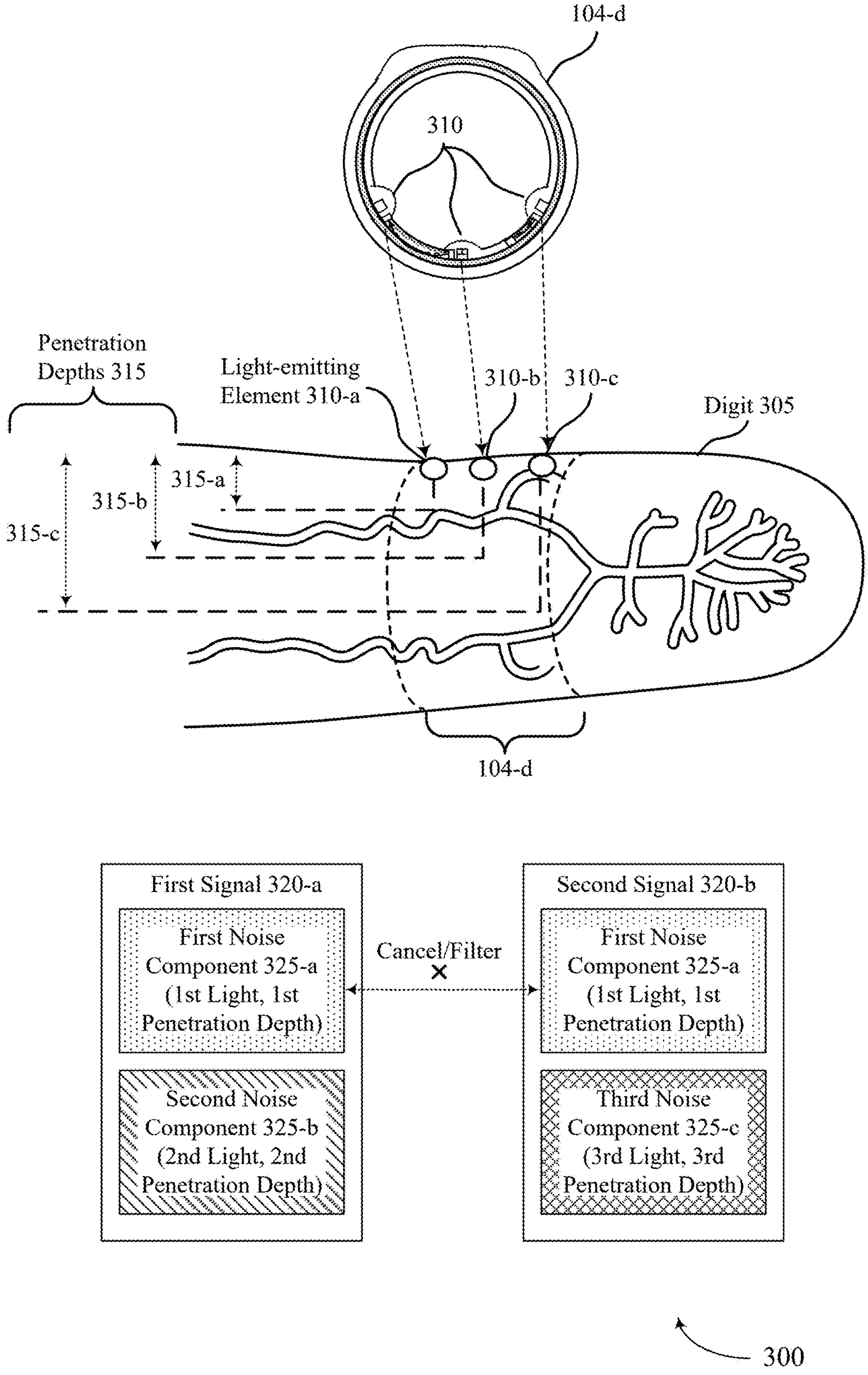
FIG. 3 shows an example of a system that supports techniques for noise reduction in accordance with aspects of the present disclosure.

FIG. 3 shows an example of a system 300 that supports techniques for wavelength-based noise reduction in accordance with aspects of the present disclosure. The system 300 may implement, or be implemented by, aspects of the system 100, the system 200, or both. The system 300 may illustrate the coupling of a wearable device 104-*d* with a human appendage or an artificial human appendage, which may be referred to as a digit 305. The wearable device 104-*d* may be placed on a human appendage (e.g., a finger) for measurements. Although the wearable device is illustrated as a ring in FIG. 3, the wearable device 104-*d* may be any example of a wearable device (e.g., a watch, necklace, bracelet, and the like). Similarly, although the digit 305 is illustrated as a finger in FIG. 3, the digit 305 may represent any human body part for any example of a wearable device 104 (e.g., a wrist for a watch, a neck for a necklace, and the like).

In some examples, the wearable device 104-*d* may include one or more light emitting elements 310. Additionally, or alternatively, the light emitting elements 310 may represent the sensors in the PPG system, the motion sensors, the temperature sensors, or the like as described with reference to FIG. 2. The light emitting elements 310 may represent LEDs, pressure sensors, thermal sensors, or the like, for detecting optical, thermal, and mechanical properties. There may be any quantity of light emitting elements 310 at any locations of the wearable device 104-*d*. The light emitting elements 310 may vary in size and distance from each other. For example, the wearable device 104-*d* may include one or more light emitting elements 310, which may be examples of LEDs, micro LEDs, mini LEDs, LDs, or any other light emitting component. For instance, a first light emitting element 310-*a* may be a first LED, a second light emitting element 310-*b* may be a second LED, and a third light emitting element 310-*c* may be a third LED. The light emitting elements 310 may make up a sensor with respective photodetectors. For example, a sensor may include a light emitting element and a photodetector.

In some cases, the wearable device 104-*d* may activate the light emitting elements 310 and perform one or more measurements, such as measurements of a physiological phenomenon of a user. Physiological phenomena that may be measured using signals collected using the light emitting components 310 (and photodetectors) may include heart rate measurements, respiration rate measurements, blood oxygen saturation measurements, HRV measurements, and the like.

As described herein, according to aspects of the present disclosure, the wearable device 104-*d* may be configured to use different combinations of light (e.g., different combinations of wavelengths) and/or different combinations of light emitting components 310 to collect signals 320 that include different noise components 325 that are associated with the penetration depths of the corresponding light wavelengths. By using different combinations of light emitting components 310 (and different wavelengths of light), the wearable device 104 may be able to compare collected signals and filter out common noise components 325 across the different signals that are attributable to common wavelengths/common light emitting elements 310 that were used to acquire the respective signals.

For the purposes of the present disclosure, the terms "signal" and "noise" may be measurement-feature-dependent, in that the dividing line between a "signal" and "noise" may be dependent on the respective physiological measurement being performed. In other words, what is considered a "signal" for one feature (e.g., physiological feature/measurement) may be considered "noise" for another feature. For example, arterial walls can reflect light due to refractive index difference between the arterial wall and surrounding tissue. The reflected light may carry or otherwise include/contain information about finger digital artery pulsation (and/or other physiological features), which can increase the AC-portion of the measured PPG and can be considered as part of "signal" for heart rate measurement. Comparatively, the same reflected light component of PPG can also be considered as "noise" for blood oxygen saturation measurements, as the light reflected from the arterial wall may not contain any information about light absorption to blood, which is the basic physical phenomena used for blood oxygen saturation measurements. As such, for blood oxygen saturation measurements, it would be beneficial to filter out (as "noise") the "arterial wall movement" component that is attributable to the light reflected from the arterial wall. However, for heart rate measurements, the same "arterial wall movement" component that is attributable to the light reflected from the arterial wall may be kept as part of the "signal" for heart rate and/or HRV measurements.

For example, the wearable device 104-*d* may emit light from a first set of light emitting elements 310. For instance, the first set of light emitting elements 310 may include a first light emitting element 310-*a* associated with a first wavelength, and a second light emitting element 310-*b* associated with a second wavelength. The second wavelength may be different than the first wavelength (e.g., the first light emitting element 310-*a* may emit a different colored light than the second light emitting element 310-*b*).

Similarly, the wearable device 104-*d* may emit light from a second set of light emitting elements 310. For instance, the second set of light emitting elements 310 may include the first light emitting element 310-*a* (e.g., a same light emitting element 310 as the first set of light emitting elements 310) associated with the first wavelength, and a third light emitting element 310-*c* associated with a third wavelength. The third wavelength may be different than the first wavelength (e.g., the first light emitting element 310-*a* may emit a different colored light than the third light emitting element 310-*c*).

In some cases, each wavelength of light may be associated with a respective penetration depth 315. Each respective penetration depth 315 may depend on the wavelength (e.g., color) of light being emitted from the light emitting element 310. For instance, the first light emitting element 310-*a* may emit a green light (e.g., a first wavelength) with a first penetration depth 315-*a*. The second light emitting element 310-*b* may emit a red light (e.g., a second wavelength) with a second penetration depth 315-*b*. The third light emitting element 310-*c* may emit an IR light (e.g., a third wavelength) with a third penetration depth 315-*c*. Although described as specific colored lights, each light emitting element 310 may emit any colored light.

In some cases, measurements/signals performed at different penetration depths 315 may include different noise components. For instance, the first penetration depth 315-*a* may be limited to a first skin layer (e.g., the epidermis). Similarly, the second penetration depth 315-*b* may be limited to a second skin layer (e.g., the hypodermis). Moreover, different penetration depths 315 may include or reach different physiological structures, such as capillaries, veins, arteries, bones, and the like. In this regard, each layer of tissue (e.g., each penetration depth) may include or be associated with different noise components 325. For example, a first wavelength of light reaching an artery may be affected by different causes of noise as compared to a second wavelength of light that only reaches layers of tissue that do not include arteries.

Moreover, the varying penetration depths 315 may result in certain wavelengths of light being more or less susceptible to motion artifacts. Motion artifacts are a type of noise experienced in PPG signals that may result from movement of the user (and/or movement of the wearable device 104 relative to the tissue/skin). For example, red light may be more susceptible to motion artifacts as compared to green light.

In some cases, the wearable device 104-*d* may measure one or more signals 320-*a*, 320-*b* representing one or more physiological phenomena using the respective sets of light emitting components 310. For example, the first set of light emitting elements 310 (e.g., green+red) may be used to acquire a first signal 320-*a* by simultaneously (or substantially simultaneously) emitting green and red light into the tissue of the user. Similarly, the second set of light emitting components 310 (e.g., green+IR) may be used to acquire a second signal 320-*b* by simultaneously (or substantially simultaneously) emitting green and IR light into the tissue of the user. The respective signals 320 may include or be associated with one or more physiological phenomena. Some examples of the physiological phenomenon that may be measured/indicated by the signals 320 may include heart rate measurements of the user, an oxygen saturation level (e.g., SpO2), blood oxygen levels, a blood pressure, or any combination thereof.

In addition to carrying information associated with one or more physiological phenomenon (e.g., heart rate information, blood oxygen information, etc.), each of the respective signals 320 may additionally include noise components 325 that are associated with (e.g., attributable) to the wavelengths of light (and corresponding penetration depths 315) used to acquire the respective signals 320. For example, as shown in FIG. 3, the first signal 320-*a* may include a first representation of one or more physiological phenomenon, a first noise component 325-*a*, and a second noise component 325-*b*. The first noise component 325-*a* may be associated with (e.g., attributable to) noise experienced by green light (first light) that penetrates to a first penetration depth 315-*a*, where the second noise component 325-*b* may be associated with (e.g., attributable to) noise experienced by red light (second light) that penetrates to a second penetration depth 315-*b*.

Similarly, the second signal 320-*b* may include a second representation of one or more physiological phenomena, the first noise component 325-*a*, and a third noise component 325-*c*. The first noise component 325-*a* may be associated with (e.g., attributable to) noise experienced by green light (first light) that penetrates to the first penetration depth 315-*a*, where the third noise component 325-*c* may be associated with (e.g., attributable to) noise experienced by IR light (third light) that penetrates to a third penetration depth 315-*c*.

In this regard, the first noise component 325-*a* may be a common noise component based on the first penetration depth 315-*a* associated with the first wavelength, which was used to acquire both the first signal 320-*a* and the second signal 320-*b*. In other words, when green light is used to collect both the first signal 320-*a* and the second signal

320-*b*, both signals may include a common noise component 325 (e.g., first noise component 325-*a*) that is attributable to the first penetration depth 315-*a* of green light.

Continuing with the same example, the wearable device 104-*d* may be configured to filter one or more noise components 325 from the respective signals 320, which may lead to more accurate and reliable signals 320. For example, the first signal 320-*a* and the second signal 320-*b* may undergo a noise filtering process (e.g., post-processing). As part of the noise filtering process/procedure, the wearable device 104-*d* may compare the first signal 320-*a* and the second signal 320-*b* (e.g., compare the different physiological measurements) to determine/identify the one or more noise components 325. That is, the wearable device 104-*d* may identify different noise components 325 that are attributable (e.g., associated with) respective wavelengths/penetration depths 315.

In some aspects, the wearable device 104-*d* may identify a common noise component 325 across the respective signals 320, and may remove the common noise components 325. For example, as shown in FIG. 3, the wearable device 104-*d* may cancel, filter, or otherwise remove the first noise component 325-*a* from the first signal 320-*a* and the second signal 320-*b* based on the differences between the physiological measurements and their associated penetration depths 315. In other words, the wearable device 104-*d* may compare the signals 320-*a*, 320-*b* to identify a common denominator effect of the green light used for the respective signals 320, and may remove/filter the common noise component 325-*a* from the signals (thereby reducing or eliminating an effect of noise resulting from the green light used for the signals 320-*a*, 320-*b*).

As a specific example, if the first light emitting element 310-*a* emits a green colored light (e.g., a green light signal that models skin-ring motion), removing the contribution of the green light from the first signal 320-*a* (e.g., green+red signal) and the second signal 320-*b* (e.g., green+IR signal) may remove the first noise component 325-*a* from the respective signals 320, thereby reducing or eliminating one or more motion artifacts associated with motion of the wearable device 104-*d*.

In some cases, the wearable device 104-*d* may calculate a third signal, which may be referred to as a "clean" signal. For instance, the wearable device 104-*d* may calculate the third signal based on removing the first noise component 325-*a* from the first signal 320-*a* and the second signal 320-*b*. In this regard, motion artifacts attributable to the first noise component 325-*a* may be removed (or otherwise reduced/mitigated) from the third signal. As such, in some cases, the third signal may be used to perform more accurate or more reliable physiological measurements.

In some aspects, the process described herein may be performed iteratively multiple times using different combinations of light in order to identify common noise components 325 associated with different wavelengths/penetration depths. For example, a first iteration may be used by utilizing green light as a common denominator between two signals 320 in order to identify/filter noise attributable to green light. Subsequently, a second iteration may be used by utilizing red light as a common denominator between two signals 320 in order to identify/filter noise attributable to red light.

While much of the present disclosure is described in the context of green, red, and IR light, other wavelengths of light may be used, such as blue light, yellow light, UV light, and the like. For example, in some cases, a light emitting element 310 may emit a blue light (e.g., wavelength of approximately 420 nm) which may reach the top epidermis layer (e.g., that does not contain arteries or pulsation). Additionally, or alternatively, a light emitting element 310 may emit a green light (e.g., wavelength of approximately 530 nm) which may be used in heart rate measurements from the dermis layer. The blue light signal may include mostly motion artifacts coming from sensor movement in respect to skin. The green light signal may include both movements artifacts and pulsating heart rate signals. In some instances, removing the blue signal components (e.g., noise components 325 attributable to blue light) from green signals may remove some of the motion artifacts and improve the heart rate signal quality.

In some cases, a light emitting element 310 may emit an ultraviolet (UV) light (e.g., wavelength of approximately 350 nm to 400 nm) which may reach the top stratum corneum-layer of skin epidermis. The UV light signal may include signal artifacts that come from a superficial skin layer. Additionally, or alternatively, the UV light signal may include signal artifacts as a pure reflection from the top of the skin. In some instances, a wavelength may reach one or more physiological structures inside the finger (e.g., bone, nerves, fat, sinews) at different penetration depths 315 that may have a particular spectral response. In these instances, the physiological structures may be detected separately with specific (laser) wavelengths in case they move or mask the wanted optical signals.

Figure 4:
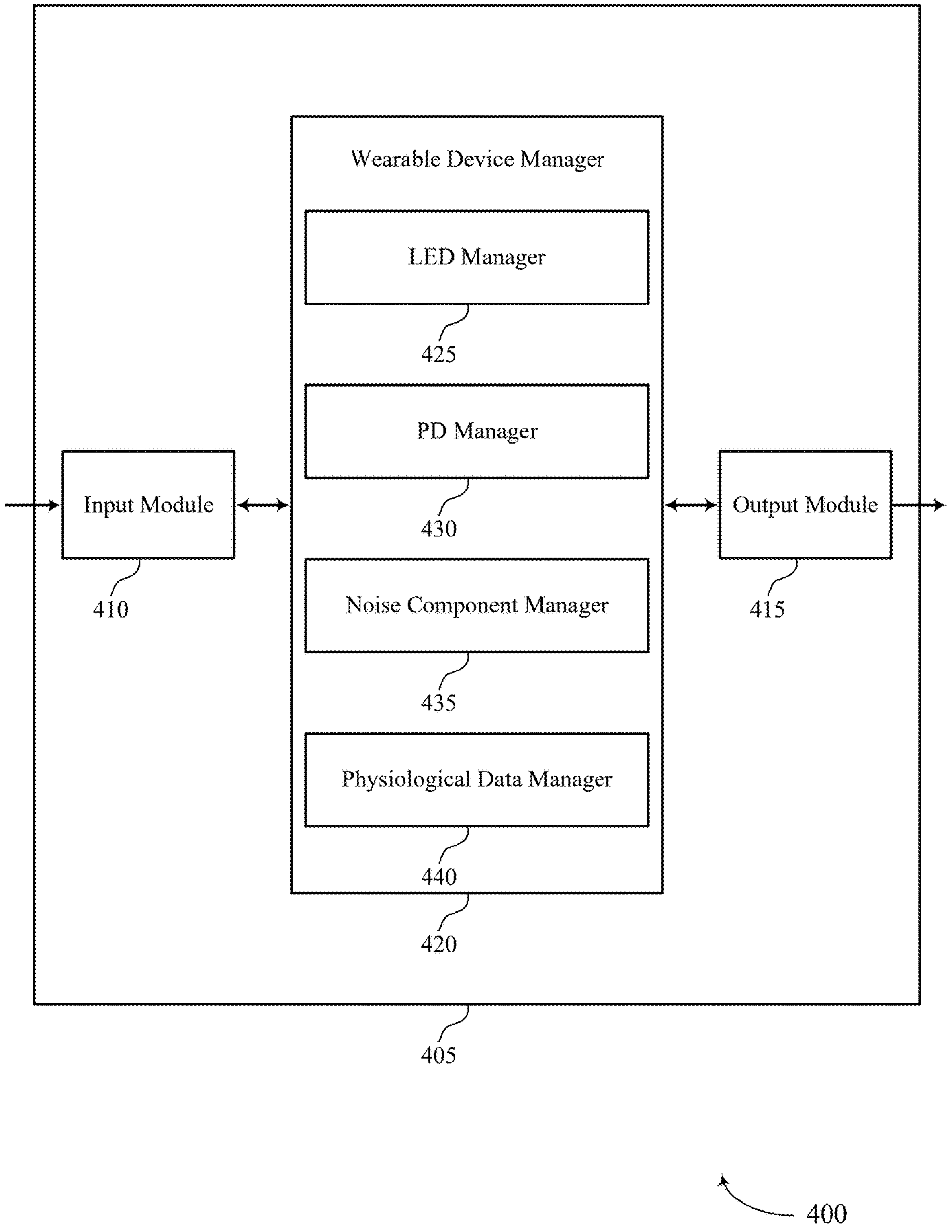
FIG. 4 shows a block diagram of an apparatus that supports techniques for noise reduction in accordance with aspects of the present disclosure.

FIG. 4 shows a block diagram 400 of a device 405 that supports techniques for noise reduction in accordance with aspects of the present disclosure. The device 405 may include an input module 410, an output module 415, and a wearable device manager 420. The device 405, or one of more components of the device 405 (e.g., the input module 410, the output module 415, and the wearable device manager 420), may include at least one processor, which may be coupled with at least one memory, to support the described techniques. Each of these components may be in communication with one another (e.g., via one or more buses).

For example, the wearable device manager 420 may include a LED manager 425, a PD manager 430, a noise component manager 435, a physiological data manager 440, or any combination thereof. In some examples, the wearable device manager 420, or various components thereof, may be configured to perform various operations (e.g., receiving, monitoring, transmitting) using or otherwise in cooperation with the input module 410, the output module 415, or both. For example, the wearable device manager 420 may receive information from the input module 410, send information to the output module 415, or be integrated in combination with the input module 410, the output module 415, or both to receive information, transmit information, or perform various other operations as described herein.

The wearable device manager 420 may support noise filtering for a wearable ring device in accordance with examples as disclosed herein. The LED manager 425 may be configured as or otherwise support a means for emitting light from a first set of light emitting elements of the wearable ring device, wherein the first set of light emitting elements comprises at least a first light emitting element associated with a first wavelength and a second light emitting element associated with a second wavelength different than the first wavelength. The LED manager 425 may be configured as or otherwise support a means for emitting light from a second set of light emitting elements of the wearable ring device, wherein the second set of light emitting elements comprises at least the first light emitting element and a third light emitting element associated with a third wavelength. The PD manager 430 may be configured as or otherwise support a means for measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength. The PD manager 430 may be configured as or otherwise support a means for measuring a second signal comprising a second representation of one or more physiological phenomenon, the first noise component, and a third noise component from the second set of light emitting elements, wherein the third noise component is based at least in part on a third penetration depth association with the third wavelength. The noise component manager 435 may be configured as or otherwise support a means for removing the first noise component from the first signal and the second signal based at least in part on comparing the first signal and the second signal. The physiological data manager 440 may be configured as or otherwise support a means for calculating a third signal based at least in part on removing the first noise component from the first signal and the second signal.

Figure 5:
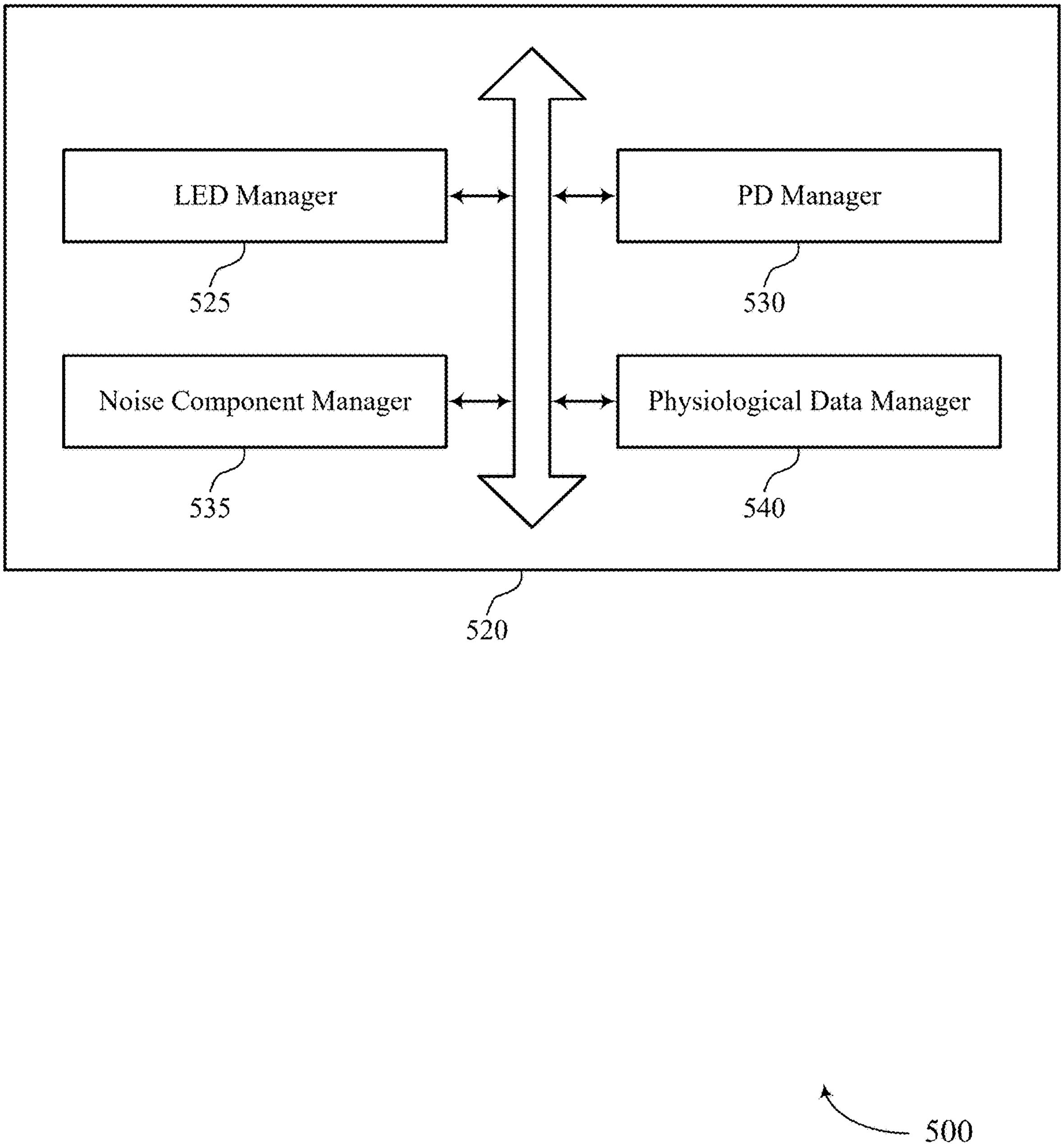
FIG. 5 shows a block diagram of a wearable device manager that supports techniques for noise reduction in accordance with aspects of the present disclosure.

FIG. 5 shows a block diagram 500 of a wearable device manager 520 that supports techniques for noise reduction in accordance with aspects of the present disclosure. The wearable device manager 520 may be an example of aspects of a wearable device manager or a wearable device manager 420, or both, as described herein. The wearable device manager 520, or various components thereof, may be an example of means for performing various aspects of techniques for noise reduction as described herein. For example, the wearable device manager 520 may include a LED manager 525, a PD manager 530, a noise component manager 535, a physiological data manager 540, or any combination thereof. Each of these components, or components of subcomponents thereof (e.g., one or more processors, one or more memories), may communicate, directly or indirectly, with one another (e.g., via one or more buses).

The wearable device manager 520 may support noise filtering for a wearable ring device in accordance with examples as disclosed herein. The LED manager 525 may be configured as or otherwise support a means for emitting light from a first set of light emitting elements of the wearable ring device, wherein the first set of light emitting elements comprises at least a first light emitting element associated with a first wavelength and a second light emitting element associated with a second wavelength different than the first wavelength. In some examples, the LED manager 525 may be configured as or otherwise support a means for emitting light from a second set of light emitting elements of the wearable ring device, wherein the second set of light emitting elements comprises at least the first light emitting element and a third light emitting element associated with a third wavelength. The PD manager 530 may be configured as or otherwise support a means for measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength. In some examples, the PD manager 530 may be configured as or otherwise support a means for measuring a second signal comprising a second representation of one or more physiological phenomenon, the first noise component, and a third noise component from the second set of light emitting elements, wherein the third noise component is based at least in part on a third penetration depth association with the third wavelength. The noise component manager 535 may be configured as or otherwise support a means for removing the first noise component from the first signal and the second signal based at least in part on comparing the first signal and the second signal. The physiological data manager 540 may be configured as or otherwise support a means for calculating a third signal based at least in part on removing the first noise component from the first signal and the second signal.

In some examples, the first penetration depth is substantially limited to a dermis skin layer of a finger and the second penetration depth substantially reaches an artery within a hypodermis skin layer of the finger.

In some examples, the first penetration depth is substantially limited to an epidermis skin layer of a finger and the second penetration depth substantially reaches a dermis skin layer of the finger.

In some examples, the first light emitting element comprises a first LED, the second light emitting element comprises a second LED, and the third light emitting element comprises a third LED.

In some examples, the first wavelength comprises green light, the second wavelength comprises red light, and the third wavelength comprises IR light.

In some examples, the one or more physiological phenomenon comprises blood oxygen levels, heart rate measurements, or both.

In some examples, the first noise component corresponds with motion artifacts associated with motion of the wearable ring device.

Figure 6:
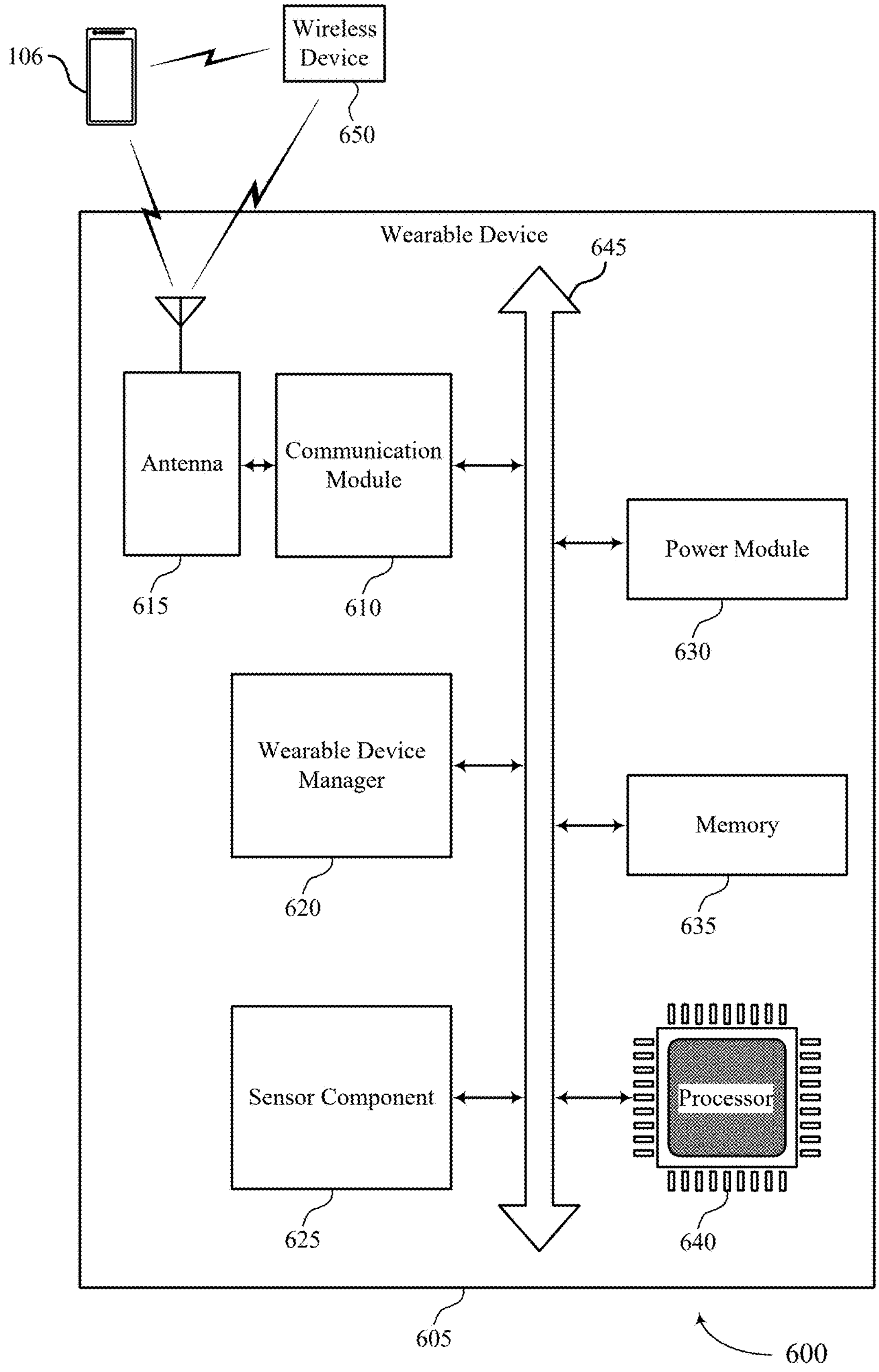
FIG. 6 shows a diagram of a system including a device that supports techniques for noise reduction in accordance with aspects of the present disclosure.

FIG. 6 shows a diagram of a system 600 including a device 605 that supports techniques for noise reduction in accordance with aspects of the present disclosure. The device 605 may be an example of or include the components of a device 405 as described herein. The device 605 may include an example of a wearable device 104, as described previously herein. The device 605 may include components for bi-directional communications including components for transmitting and receiving communications with a user device 106 and a server 110, such as a wearable device manager 620, a communication module 610, an antenna 615, a sensor component 625, a power module 630, at least one memory 635, at least one processor 640, and a wireless device 650. These components may be in electronic communication or otherwise coupled (e.g., operatively, communicatively, functionally, electronically, electrically) via one or more buses (e.g., a bus 645).

The wearable device manager 620 may support noise filtering for a wearable ring device in accordance with examples as disclosed herein. For example, the wearable device manager 620 may be configured as or otherwise support a means for emitting light from a first set of light emitting elements of the wearable ring device, wherein the first set of light emitting elements comprises at least a first light emitting element associated with a first wavelength and a second light emitting element associated with a second wavelength different than the first wavelength. The wearable device manager 620 may be configured as or otherwise support a means for emitting light from a second set of light emitting elements of the wearable ring device, wherein the second set of light emitting elements comprises at least the first light emitting element and a third light emitting element associated with a third wavelength. The wearable device manager 620 may be configured as or otherwise support a means for measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength. The wearable device manager 620 may be configured as or otherwise support a means for measuring a second signal comprising a second representation of one or more physiological phenomenon, the first noise component, and a third noise component from the second set of light emitting elements, wherein the third noise component is based at least in part on a third penetration depth association with the third wavelength. The wearable device manager 620 may be configured as or otherwise support a means for removing the first noise component from the first signal and the second signal based at least in part on comparing the first signal and the second signal. The wearable device manager 620 may be configured as or otherwise support a means for calculating a third signal based at least in part on removing the first noise component from the first signal and the second signal.

Figure 7:
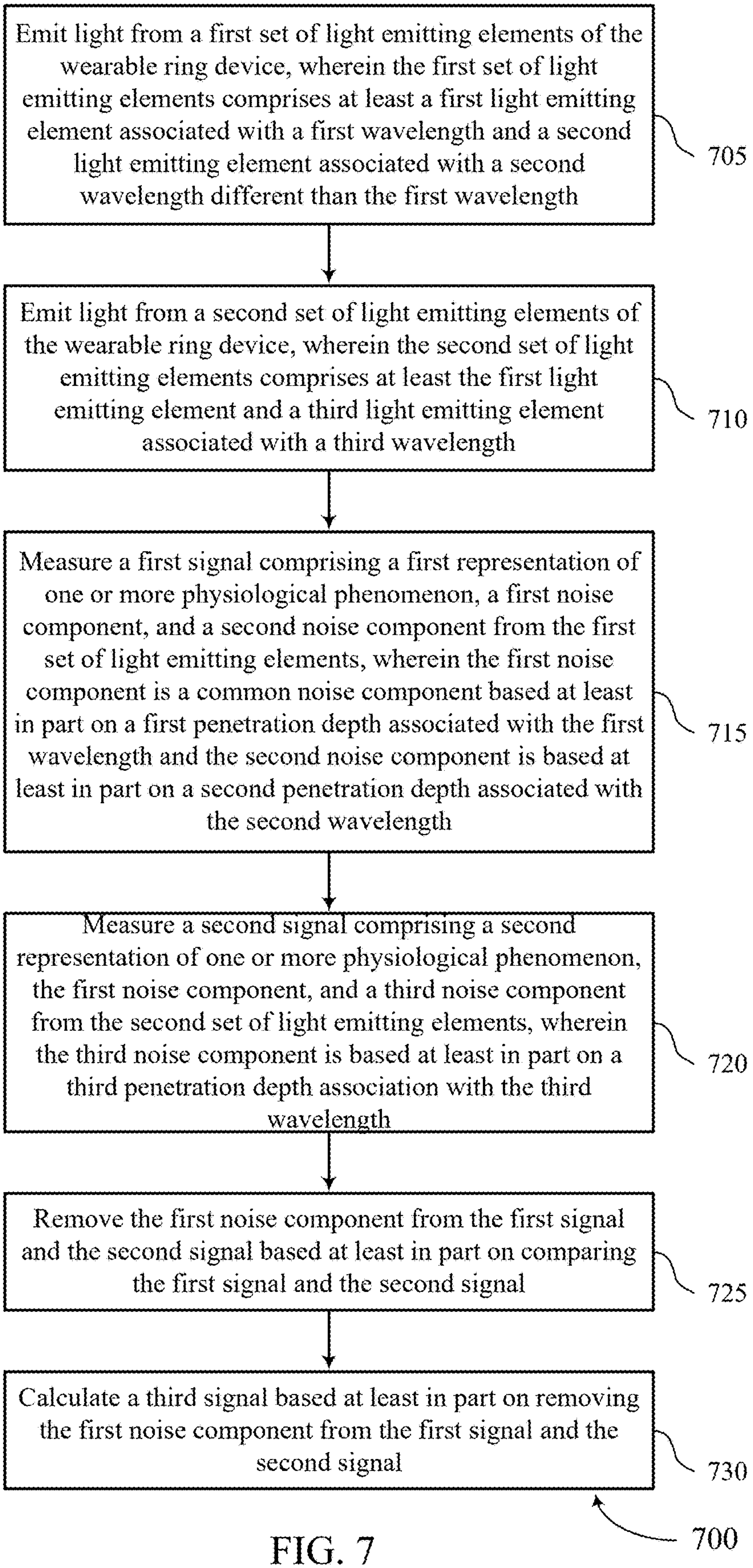
FIG. 7 shows a flowchart illustrating methods that support techniques for noise reduction in accordance with aspects of the present disclosure.

FIG. 7 shows a flowchart illustrating a method 700 that supports techniques for noise reduction in accordance with aspects of the present disclosure. The operations of the method 700 may be implemented by a wearable device or its components as described herein. For example, the operations of the method 700 may be performed by a wearable device as described with reference to FIGS. 1 through 6. In some examples, a wearable device may execute a set of instructions to control the functional elements of the wearable device to perform the described functions. Additionally, or alternatively, the wearable device may perform aspects of the described functions using special-purpose hardware.

At 705, the method may include emitting light from a first set of light emitting elements of the wearable ring device, wherein the first set of light emitting elements comprises at least a first light emitting element associated with a first wavelength and a second light emitting element associated with a second wavelength different than the first wavelength. The operations of block 705 may be performed in accordance with examples as disclosed herein. In some examples, aspects of the operations of 705 may be performed by a LED manager 525 as described with reference to FIG. 5.

At 710, the method may include emitting light from a second set of light emitting elements of the wearable ring device, wherein the second set of light emitting elements comprises at least the first light emitting element and a third light emitting element associated with a third wavelength. The operations of block 710 may be performed in accordance with examples as disclosed herein. In some examples, aspects of the operations of 710 may be performed by a LED manager 525 as described with reference to FIG. 5.

At 715, the method may include measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength. The operations of block 715 may be performed in accordance with examples as disclosed herein. In some examples, aspects of the operations of 715 may be performed by a PD manager 530 as described with reference to FIG. 5.

At 720, the method may include measuring a second signal comprising a second representation of one or more physiological phenomenon, the first noise component, and a third noise component from the second set of light emitting elements, wherein the third noise component is based at least in part on a third penetration depth association with the third wavelength. The operations of block 720 may be performed in accordance with examples as disclosed herein. In some examples, aspects of the operations of 720 may be performed by a PD manager 530 as described with reference to FIG. 5.

At 725, the method may include removing the first noise component from the first signal and the second signal based at least in part on comparing the first signal and the second signal. The operations of block 725 may be performed in accordance with examples as disclosed herein. In some examples, aspects of the operations of 725 may be performed by a noise component manager 535 as described with reference to FIG. 5.

At 730, the method may include calculating a third signal based at least in part on removing the first noise component from the first signal and the second signal. The operations of block 730 may be performed in accordance with examples as disclosed herein. In some examples, aspects of the operations of 730 may be performed by a physiological data manager 540 as described with reference to FIG. 5.

It should be noted that the methods described above describe possible implementations, and that the operations and the steps may be rearranged or otherwise modified and that other implementations are possible. Furthermore, aspects from two or more of the methods may be combined.

A method for noise filtering for a wearable ring device by an apparatus is described. The method may include emitting light from a first set of light emitting elements of the wearable ring device, wherein the first set of light emitting elements comprises at least a first light emitting element associated with a first wavelength and a second light emitting element associated with a second wavelength different than the first wavelength, emitting light from a second set of light emitting elements of the wearable ring device, wherein the second set of light emitting elements comprises at least the first light emitting element and a third light emitting element associated with a third wavelength, measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength, measuring a second signal comprising a second representation of one or more physiological phenomenon, the first noise component, and a third noise component from the second set of light emitting elements, wherein the third noise component is based at least in part on a third penetration depth association with the third wavelength, removing the first noise component from the first signal and the second signal based at least in part on comparing the first signal and the second signal, and calculating a third signal based at least in part on removing the first noise component from the first signal and the second signal.

An apparatus for noise filtering for a wearable ring device is described. The apparatus may include one or more memories storing processor executable code, and one or more processors coupled with the one or more memories. The one or more processors may individually or collectively operable to execute the code to cause the apparatus to emit light from a first set of light emitting elements of the wearable ring device, wherein the first set of light emitting elements comprises at least a first light emitting element associated with a first wavelength and a second light emitting element associated with a second wavelength different than the first wavelength, emit light from a second set of light emitting elements of the wearable ring device, wherein the second set of light emitting elements comprises at least the first light emitting element and a third light emitting element associated with a third wavelength, measure a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength, measure a second signal comprising a second representation of one or more physiological phenomenon, the first noise component, and a third noise component from the second set of light emitting elements, wherein the third noise component is based at least in part on a third penetration depth association with the third wavelength, remove the first noise component from the first signal and the second signal based at least in part on comparing the first signal and the second signal, and calculate a third signal based at least in part on removing the first noise component from the first signal and the second signal.

Another apparatus for noise filtering for a wearable ring device is described. The apparatus may include means for emitting light from a first set of light emitting elements of the wearable ring device, wherein the first set of light emitting elements comprises at least a first light emitting element associated with a first wavelength and a second light emitting element associated with a second wavelength different than the first wavelength, means for emitting light from a second set of light emitting elements of the wearable ring device, wherein the second set of light emitting elements comprises at least the first light emitting element and a third light emitting element associated with a third wavelength, means for measuring a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength, means for measuring a second signal comprising a second representation of one or more physiological phenomenon, the first noise component, and a third noise component from the second set of light emitting elements, wherein the third noise component is based at least in part on a third penetration depth association with the third wavelength, means for removing the first noise component from the first signal and the second signal based at least in part on comparing the first signal and the second signal, and means for calculating a third signal based at least in part on removing the first noise component from the first signal and the second signal.

A non-transitory computer-readable medium storing code for noise filtering for a wearable ring device is described. The code may include instructions executable by one or more processors to emit light from a first set of light emitting elements of the wearable ring device, wherein the first set of light emitting elements comprises at least a first light emitting element associated with a first wavelength and a second light emitting element associated with a second wavelength different than the first wavelength, emit light from a second set of light emitting elements of the wearable ring device, wherein the second set of light emitting elements comprises at least the first light emitting element and a third light emitting element associated with a third wavelength, measure a first signal comprising a first representation of one or more physiological phenomenon, a first noise component, and a second noise component from the first set of light emitting elements, wherein the first noise component is a common noise component based at least in part on a first penetration depth associated with the first wavelength and the second noise component is based at least in part on a second penetration depth associated with the second wavelength, measure a second signal comprising a second representation of one or more physiological phenomenon, the first noise component, and a third noise component from the second set of light emitting elements, wherein the third noise component is based at least in part on a third penetration depth association with the third wavelength, remove the first noise component from the first signal and the second signal based at least in part on comparing the first signal and the second signal, and calculate a third signal based at least in part on removing the first noise component from the first signal and the second signal.

In some examples of the method, apparatus, and non-transitory computer-readable medium described herein, the first penetration depth may be substantially limited to a dermis skin layer of a finger and the second penetration depth substantially reaches an artery within a hypodermis skin layer of the finger.

In some examples of the method, apparatus, and non-transitory computer-readable medium described herein, the first penetration depth may be substantially limited to an epidermis skin layer of a finger and the second penetration depth substantially reaches a dermis skin layer of the finger.

In some examples of the method, apparatus, and non-transitory computer-readable medium described herein, the first light emitting element comprises a first LED, the second light emitting element comprises a second LED, and the third light emitting element comprises a third LED.

In some examples of the method, apparatus, and non-transitory computer-readable medium described herein, the first wavelength comprises green light, the second wavelength comprises red light, and the third wavelength comprises IR light.

In some examples of the method, apparatus, and non-transitory computer-readable medium described herein, the one or more physiological phenomenon comprises blood oxygen levels, heart rate measurements, or both.

In some examples of the method, apparatus, and non-transitory computer-readable medium described herein, the first noise component corresponds with motion artifacts associated with motion of the wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as IR, radio, and microwave, then the coaxial cable, fiber optic cable, twisted pair, DSL, or wireless technologies such as IR, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for noise filtering for a wearable ring device, comprising:

emitting first light from a first set of light emitting elements of the wearable ring device, the first light associated with a first wavelength and a second wavelength, wherein the first set of light emitting elements comprises at least a first light emitting element associated with the first wavelength and a second light emitting element associated with the second wavelength different than the first wavelength;

emitting second light from a second set of light emitting elements of the wearable ring device, the second light associated with the first wavelength and a third wavelength, wherein the second set of light emitting elements comprises at least the first light emitting element and a third light emitting element associated with the third wavelength;

measuring a first signal based at least in part on the first light, the first signal comprising a first representation of one or more physiological phenomenon, a first noise component, and a second noise component, wherein the first noise component is based at least in part on a first penetration depth associated with the first wavelength and the second noise component is based at least in part on a second penetration depth associated with the second wavelength;

measuring a second signal based at least in part on the second light, the second signal comprising a second representation of the one or more physiological phenomenon, the first noise component, and a third noise component, wherein the third noise component is based at least in part on a third penetration depth association with the third wavelength, wherein the first noise component is a common noise component across the first signal and the second signal that is based at least in part on the first wavelength;

removing the first noise component from the first signal and the second signal based at least in part on comparing the first signal and the second signal; and calculating a third signal based at least in part on removing the first noise component from the first signal and the second signal.

2. The method of claim 1, wherein the first penetration depth is substantially limited to a dermis skin layer of a finger and the second penetration depth substantially reaches an artery within a hypodermis skin layer of the finger.

3. The method of claim 1, wherein the first penetration depth is substantially limited to an epidermis skin layer of a finger and the second penetration depth substantially reaches a dermis skin layer of the finger.

4. The method of claim 1, wherein the first light emitting element comprises a first light emitting diode (LED), the second light emitting element comprises a second LED, and the third light emitting element comprises a third LED.

5. The method of claim 4, wherein the first wavelength comprises green light, the second wavelength comprises red light, and the third wavelength comprises infrared light.

6. The method of claim 1, wherein the one or more physiological phenomenon comprises blood oxygen levels, heart rate measurements, or both.

7. The method of claim 1, wherein the first noise component corresponds with motion artifacts associated with motion of the wearable ring device.

8. A system for noise filtering for a wearable ring device, comprising:

one or more memories storing processor-executable code; and one or more processors coupled with the one or more memories and individually or collectively operable to execute the code to:

emit first light from a first set of light emitting elements of the wearable ring device, the first light associated with a first wavelength and a second wavelength, wherein the first set of light emitting elements comprises at least a first light emitting element associated with the first wavelength and a second light emitting element associated with the second wavelength different than the first wavelength;

emit second light from a second set of light emitting elements of the wearable ring device, the second light associated with the first wavelength and a third wavelength, wherein the second set of light emitting elements comprises at least the first light emitting element and a third light emitting element associated with the third wavelength;

measure a first signal based at least in part on the first light, the first signal comprising a first representation of one or more physiological phenomenon, a first noise component, and a second noise component, wherein the first noise component is based at least in part on a first penetration depth associated with the first wavelength and the second noise component is based at least in part on a second penetration depth associated with the second wavelength;

measure a second signal based at least in part on the second light, the second signal comprising a second representation of the one or more physiological phenomenon, the first noise component, and a third noise component, wherein the third noise component is based at least in part on a third penetration depth association with the third wavelength, wherein the first noise component is a common noise component across the first signal and the second signal that is based at least in part on the first wavelength;

remove the first noise component from the first signal and the second signal based at least in part on comparing the first signal and the second signal; and calculate a third signal based at least in part on removing the first noise component from the first signal and the second signal.

9. The system of claim 8, wherein the first penetration depth is substantially limited to a dermis skin layer of a finger and the second penetration depth substantially reaches an artery within a hypodermis skin layer of the finger.

10. The system of claim 8, wherein the first penetration depth is substantially limited to an epidermis skin layer of a finger and the second penetration depth substantially reaches a dermis skin layer of the finger.

11. The system of claim 8, wherein the first light emitting element comprises a first light emitting diode (LED), the second light emitting element comprises a second LED, and the third light emitting element comprises a third LED.

12. The system of claim 11, wherein the first wavelength comprises green light, the second wavelength comprises red light, and the third wavelength comprises infrared light.

13. The system of claim 8, wherein the one or more physiological phenomenon comprises blood oxygen levels, heart rate measurements, or both.

14. The system of claim 8, wherein the first noise component corresponds with motion artifacts associated with motion of the wearable ring device.

15. A non-transitory computer-readable medium storing code for noise filtering for a wearable ring device, the code comprising instructions executable by one or more processors to:

emit first light from a first set of light emitting elements of the wearable ring device, the first light associated with a first wavelength and a second wavelength, wherein the first set of light emitting elements comprises at least a first light emitting element associated with the first wavelength and a second light emitting element associated with the second wavelength different than the first wavelength;

emit second light from a second set of light emitting elements of the wearable ring device, the second light associated with the first wavelength and a third wavelength, wherein the second set of light emitting elements comprises at least the first light emitting element and a third light emitting element associated with the third wavelength;

measure a first signal based at least in part on the first light, the first signal comprising a first representation of one or more physiological phenomenon, a first noise component, and a second noise component, wherein the first noise component is based at least in part on a first penetration depth associated with the first wavelength and the second noise component is based at least in part on a second penetration depth associated with the second wavelength;

measure a second signal based at least in part on the second light, the second signal comprising a second representation of the one or more physiological phenomenon, the first noise component, and a third noise component, wherein the third noise component is based at least in part on a third penetration depth association with the third wavelength, wherein the first noise component is a common noise component across the first signal and the second signal that is based at least in part on the first wavelength;

remove the first noise component from the first signal and the second signal based at least in part on comparing the first signal and the second signal; and calculate a third signal based at least in part on removing the first noise component from the first signal and the second signal.

16. The non-transitory computer-readable medium of claim 15, wherein the first penetration depth is substantially limited to a dermis skin layer of a finger and the second penetration depth substantially reaches an artery within a hypodermis skin layer of the finger.

17. The non-transitory computer-readable medium of claim 15, wherein the first penetration depth is substantially limited to an epidermis skin layer of a finger and the second penetration depth substantially reaches a dermis skin layer of the finger.

18. The non-transitory computer-readable medium of claim 15, wherein the first light emitting element comprises a first light emitting diode (LED), the second light emitting element comprises a second LED, and the third light emitting element comprises a third LED.

19. The non-transitory computer-readable medium of claim 18, wherein the first wavelength comprises green light, the second wavelength comprises red light, and the third wavelength comprises infrared light.

20. The non-transitory computer-readable medium of claim 15, wherein the one or more physiological phenomenon comprises blood oxygen levels, heart rate measurements, or both.

* * * * *